United States Patent [19]

Himel et al.

[11] 4,353,962
[45] * Oct. 12, 1982

[54] IN-FLIGHT ENCAPSULATION OF PARTICLES

[75] Inventors: Chester M. Himel, Athens, Ga.; Nathan F. Cardarelli, Akron, Ohio

[73] Assignee: Environmental Chemicals, Inc., Wauconda, Ill.

[ * ] Notice: The portion of the term of this patent subsequent to Aug. 25, 1998, has been disclaimed.

[21] Appl. No.: 264,822

[22] Filed: May 18, 1981

Related U.S. Application Data

[63] Continuation-in-part of Ser. No. 149,982, May 15, 1980, Pat. No. 4,286,020, which is a continuation of Ser. No. 922,171, Jul. 5, 1978, abandoned.

[51] Int. Cl.[3] .......................... B32B 5/16; B01J 13/00; B29C 6/00; B29C 13/00

[52] U.S. Cl. .................................... 428/407; 252/316; 264/4; 264/13

[58] Field of Search ...................... 264/4, 13; 428/407; 252/316

[56] References Cited

U.S. PATENT DOCUMENTS

| | | | |
|---|---|---|---|
| 2,972,545 | 2/1961 | Briskin | 424/45 |
| 3,007,887 | 11/1961 | Essig | 525/329 |
| 3,012,014 | 12/1961 | Woods | 525/329 |
| 3,015,128 | 1/1962 | Somerville, Jr. | 264/DIG. 37 |
| 3,242,051 | 3/1966 | Hiestand et al. | 424/78 |
| 3,265,629 | 8/1966 | Jensen | 424/31 |
| 3,336,155 | 8/1967 | Rowe | 252/316 |
| 3,544,500 | 12/1970 | Osmond et al. | 260/42.14 |
| 3,575,882 | 4/1971 | Vandegaer et al. | 424/32 |
| 3,607,776 | 9/1971 | Santo et al. | 424/32 |
| 3,639,306 | 2/1972 | Sternberg et al. | 252/316 |
| 3,681,089 | 8/1972 | Gould et al. | 424/16 |
| 3,681,248 | 8/1972 | Gould et al. | 252/403 |
| 3,749,772 | 7/1973 | Cardarelli et al. | 424/81 |
| 3,806,464 | 4/1974 | Matrick et al. | 252/316 |
| 3,830,750 | 8/1974 | Wellman | 252/316 |
| 3,872,023 | 3/1975 | Baum et al. | 252/316 |
| 3,932,602 | 1/1976 | Sweger | 424/45 |
| 3,939,099 | 2/1976 | Tusa et al. | 252/316 |
| 4,071,653 | 1/1978 | Boessler et al. | 428/407 |
| 4,107,071 | 8/1978 | Bayless | 252/316 |
| 4,187,194 | 2/1980 | Wellman et al. | 252/316 |
| 4,211,668 | 7/1980 | Tate | 252/316 |
| 4,285,720 | 8/1981 | Scher | 264/4 |
| 4,286,020 | 8/1981 | Himel et al. | 428/407 |

*Primary Examiner*—William R. Dixon, Jr.
*Attorney, Agent, or Firm*—Oldham, Oldham, Hudak & Weber Co.

[57] ABSTRACT

A method and composition for the in-flight encapsulation of particles such as insecticides, herbicides, molluscicides, acaricides, fungicides, nutrients, pheromones, odorants, fragrances, attractants, repellents, trace elements, plant regulants, and the like is disclosed. The composition comprises, by weight, from 1 to 40 percent of said particles, from 0.1 to 25 percent of a film-forming polymer and from 35 to 99 percent of a liquid which renders said polymers soluble or dispersible. Often, other compounds may be added to impart desirable properties such as other film-forming polymers, cross-linking agent film modifying agents, core agents, and adhesives to improve adhesion to a target. The particle may be in a true solution, suspended, or emulsified through the action of surfactants and/or emulsifying agents. The film-forming polymers include various acrylic polymers and interpolymers of alpha-beta olefinically unsaturated carboxylic acids and N-methylol acrylic amides, as set forth in U.S. Pat. No. 3,007,887. The molecular weight of the polymer generally determines whether the polymer-solvent phase is a solution, a colloidal dispersion, or an emulsion dispersion. Upon ejection from a spray apparatus and during flight through the intervening atmosphere, the solution or dispersion rapidly loses the solvent or carrier liquid component via evaporation, coacervation occurs, and a polymeric membrane forms about the particle. Control of the encapsulated particle size can be achieved through selection of the spray system and of the non-volatiles in the spray at the moment of droplet formation.

37 Claims, 4 Drawing Figures

FIG. 4

IN-FLIGHT ENCAPSULATION OF PARTICLES

CROSS-REFERENCE

This application is a continuation-in-part application of an application bearing U.S. Ser. No. 149,982 filed May 15, 1980 entitled "In-Flight Encapsulation of Particles," now U.S. Pat. No. 4,286,020, that application in turn being a continuation application of an application bearing U.S. Ser. No. 922,171 filed on July 5, 1978 entitled "In-Flight Encapsulation of Particles," now abandoned.

TECHNICAL FIELD

This application relates to the in-flight encapsulation of particles using film-forming polymers which are dispersible within a solvent or a carrier liquid, either as a colloidal dispersion or an emulsion dispersion. The in-flight encapsulation system may also employ core agents to alter the bulk, the solubility, and the volatility of the particle encapsulated by the film-forming polymer. Additionally, the wall system may be modified by film-modifying polymers which control core system solubility in the wall system and which control release characteristics of the wall.

BACKGROUND ART

The present invention relates to a composition of a self-encapsulating polymer-containing solution and a process for the in-flight encapsulation of particles such as insecticides, fungicides, herbicides, etc., contained therein. More specifically, the present invention relates to the in-flight encapsulation of said particles during passage between the egress of a spray apparatus and a target.

Heretofore, the encapsulation of a chemical substance within an enveloping polymeric membrane has been well recognized by the art. For example, U.S. Pat. Nos. 3,242,051, 3,265,629, 3,575,882, and 3,607,776 all relate to processes dependent upon phase separation and polycondensation reactions. Specifically, the 3,242,051 patent relates to preparing a solution of a liquid phase-forming micromolecular polymer in a first non-aqueous liquid, dispersing in said solution a plurality of individual discreet particles, adding a second liquid soluble in the first liquid, but not soluble with regard to said micromolecular polymer, whereby phase separation is induced and precoats the dispersed particles, settling the polymer-rich precoat, separating the precoated particles, suspending the precoated particles in an aqueous solution of a gel, and using phase separation so as to cause the formation of a colloidal-enriched phase and the encapsulation of each of these suspended precoated particles, and cooling.

U.S. Pat. No. 3,265,629 is similar but relates to the application of two coatings to the particles, namely a solid lipid and a polymer.

U.S. Pat. No. 2,648,609 relates to an air suspension technique wherein a sugar solution is sprayed onto a suspended item such as candy, gum, etc. Another technique heretofore utilized is the utilization of charging a first solution with ions so that the solution exhibits a specific charge, applying an opposite charge to a second solution, and then coating the first solution with the second solution via air flow.

U.S. Pat. No. 3,202,533 relates to the encapsulation of liquids by the use of a fluidized bed wherein the fluidized liquid is frozen and spray coated.

Common to all such above-described inventions and prior art processes is the utilization of multiple compounds or compositions of matter as well as the necessity of processing the encapsulated or microencapsulated article prior to usage or application. Moreover, costly and complex processing equipment as well as difficult technology is required to produce articles of a defined size and to meet mandatory environmental controls or regulations.

In contrast, the present invention relates to but a single self-encapsulating polymer-containing solution or dispersion. Moreover, the invention pertains to encapsulation of a particle phase, either liquid or solid or combined, via a polymer through in-flight encapsulation; that is, during the passage from the spraying or ejection equipment to the target substance or area, including an agricultural or forested area.

Compounds such as "PRO-TEC," manufactured by Agro-K Corporation, concentrate on the formation of a semi-permeable membrane which may spread over leaf surfaces because of its good surfactant properties. Difficulties in application of these membrane chemicals formed from hydrophilic polymers are avoided by a self-encapsulating, non-hydrophilic polymer-containing solution or dispersion of the present invention. Moreover, "PRO-TEC" is a film and does not relate to encapsulated particles.

U.S. Pat. No. 2,972,545 to Briskin; No. 3,015,128 to Somerville; No. 3,681,089 to Gould; No. 3,681,248 to Gould; No. 3,932,602 to Sweger; and No. 3,939,099 to Tusa relate to membrane formation, and the like, and are not pertinent concerning in-flight encapsulation of particles.

DISCLOSURE OF INVENTION

It is, therefore, an object of the present invention to provide a composition and process for the in-flight encapsulation of particles.

It is another object of the present invention to provide for the in-flight encapsulation of particles, as above, wherein said composition comprises generally a film-forming polymer in a solvent system for solubilizing said polymer, and any desired particles which may be soluble or dispersed in the solvent medium.

It is a further object of the present invention to provide for the in-flight encapsulation of particles, as above, wherein upon ejection from a spray apparatus and during flight through the intervening earth's atmosphere, the solution rapidly loses the solvent component through evaporation with coacervation occurring and resulting in the formation of a polymer membrane about the particle.

It is another object of the present invention to provide for the in-flight encapsulation of particles, as above, wherein said composition comprises generally a film-forming polymer in a solvent or carrier liquid component for dispersing, by colloidal or emulsion system, said polymer, and any desired particles which may be soluble or dispersed in the combined polymer-solvent-carrier system.

It is yet another object of the present invention to provide a film-modifying polymer in addition to the film-forming polymer in which the film-modifying polymer changes the stability and release characteristics of the encapsulating wall.

It is a further object of the present invention to provide for the in-flight encapsulation of particles, as above, wherein said particle is encapsulated by said polymer upon the evaporation of some or most, if not all, of the solvent in the process of passage of said particle between an ejector or a spray apparatus and a target.

It is an additional object of the present invention to provide for the in-flight encapsulation of particles, as above, wherein said particles are very small so that a microencapsulated product is produced.

It is a still further object of the present invention to provide for the in-flight encapsulation of particles, as above, wherein said encapsulated product is of fairly uniformed particle size.

It is a still further object of the present invention to provide for the in-flight encapsulation of particles, as above, wherein an outer polymer membrane exists about an inner particle core.

It is a still additional object of the present invention to provide for the in-flight encapsulation of particles, as above, wherein, due largely to the uniform product size, target specificity can be incorporated into the in-flight system.

It is yet another object of the present invention to provide for the in-flight encapsulation of particles, as above, wherein said encapsulated particle can be insecticides, acaricides, fungicides, herbicides, nutrients, trace minerals, nematicides, molluscicides, pheromones, odorants, fragrances, attractants, repellents, and any other desired particle.

It is yet another object of the present invention to provide for the in-flight encapsulation of particles, as above, wherein the leaching of said particle on a target instead of occurring in a matter of minutes or hours can range from a day to a period of months.

It is yet another object of the present invention to provide for the in-flight encapsulation of particles, as above, wherein crosslinking agents may be added to said solution to control the leaching time period.

It is yet another object of the present invention to provide for the in-flight encapsulation of particles, as above, wherein various adhesive and film-modifying agents may be added to said solution so that improved adhesion of said encapsulated product to said target occurs.

It is yet another object of the present invention to provide for the in-flight encapsulation of particles, as above, wherein various core agents may be added to provide secondary bulk to the core, to control the volatility of the particle, and to control the solubility of the particle with the film-forming polymer.

In general, a process for the in-flight encapsulation of particles, comprises the steps of:

(a) preparing a self-encapsulating polymer-containing dispersion;

said dispersion comprising by weight from about 0.1 percent to about 25 percent of a film-forming polymer capable of encapsulating a particle by coacervation, from about 35 percent to about 99 percent of a liquid, said liquid being a compound which will disperse said polymer, and from about 1 percent to about 40 percent of particles, or from about 0.01 percent to about 40 percent when said particle is a pheromone, said particle being soluble or dispersible in said solvent;

in situ encapsulating said soluble or dispersible particle by:

spraying into the earth's atmosphere said dispersion containing said soluble or dispersible particle from a spray apparatus, and immediately thereafter;

evaporating said solvent in said earth's atmosphere and coacervating during the passage from said spraying apparatus to an earth target said polymer and said particle in said earth's atmosphere so that said polymer substantially encapsulates said particle; and concurrently and directly applying said encapsulated particle to an earth target.

Generally, an in situ self-encapsulating polymer-containing formulation for concurrent and direct application to an earth target, comprises:

a self-encapsulating polymer containing dispersion; said dispersion comprising by weight from about 0.1 percent to about 25 percent of a film-forming polymer capable of encapsulating a particle by coacervation, from about 35 percent to about 99 percent of a liquid, and from about 1 percent to about 40 percent of a particle or from about 0.01 percent to about 40 percent when said particle is a pheromone, said particle being soluble or dispersible in said liquid, said liquid being a compound in which said polymer is dispersible.

In general, an encapsulated particle having been in situ encapsulated and concurrently and directly adhered to an earth target, comprises:

a core system and a wall system, said wall system comprising a polymer film encapsulating said core system;

said core system comprising a particle and a core agent.

In general, an encapsulated particle having been in situ encapsulated and concurrently and directly adhered to an earth target, comprises:

a particle system and a wall system, said wall system comprising a polymer film encapsulating said core system, said polymer film having been made from a colloidal or an emulsion dispersion type polymer.

In general, an in situ self-encapsulating polymeric containing formulation for concurrent and direct application to an earth target, comprising, by weight, based upon the total weight of said formulation from about 0.1 percent to about 25 percent of a film-forming polymer capable of encapsulating a particle by coacervation, from about 35 percent to about 99 percent of a liquid, and from about 1 percent to about 40 percent of a particle or from about 0.01 percent to about 40 percent when said particle is a pheromone, said particle being soluble or dispersible in said liquid, said liquid being a compound in which said polymer is soluble, and from about 1 percent to about 40 percent by weight of a core agent.

In general, a process for the in situ encapsulation of particles between a spraying apparatus and an earth target, comprises the steps of:

(a) preparing a self-encapsulating polymer-containing solution;

said solution comprising by weight from about 0.1 percent to about 25 percent of a film-forming polymer capable of encapsulating a particle by coacervation, from about 35 percent to about 99 percent of a liquid, said liquid being a compound which will dissolve said polymer, and from about 1 percent to about 40 percent of particles, or from about 0.01 percent to about 40 percent when said particle is a pheromone, said particle being soluble or dispersible in said solvent;

in situ encapsulating said soluble or dispersible particle by:

spraying into the earth's atmosphere said dispersion containing said soluble or dispersible particle from a spray apparatus, and immediately thereafter;

evaporating said solvent in said earth's atmosphere and coacervating during the passage from said spraying apparatus to an earth target said polymer and said particle in said earth's atmosphere so that said polymer substantially encapsulates said particle, and concurrently and directly applying said encapsulated particle to an earth target.

BEST MODE FOR CARRYING OUT THE INVENTION

The concepts of the present invention relate to a composition and process with regard to the in-flight encapsulation of particles. Numerous applications exist through conventional ejection equipment such as conventional spraying apparatus to apply encapsulated particles for various utilities, for example, public health protection, agricultural applications, and any other area or field in which the encapsulation of particles, especially micro-encapsulation, is desired. By the term "in-flight encapsulation" it is meant that the particle is covered, surrounded, coated, or encapsulated by a film-forming polymer by a coacervation process during or between the passage from an ejector or a spraying apparatus to a desired earth (Biota) target, material, area, plant, or the like. That is, the particle is encapsulated into the earth's atmosphere and not in a spray apparatus tank, or the like, and is directly applied to a plant, forest, soil, building, etc. As such, the film is created in situ during flight as the solvent or carrier liquid of the colloidal dispersion or the emulsion dispersion system evaporates. Moreover, the encapsulated material of the present invention results in a controlled release of the particle through a leaching mechanism so that in effect a slow release of the particle is achieved from a matter of a day or two to several weeks or months.

The film-forming polymer is a component within the polymer-solvent system. Depending upon the molecular weight of the film-forming polymer, the polymer-solvent system may be a solution, a colloidal dispersion, or an emulsion dispersion. When the molecular weight of the film-forming polymer is too large for the polymer to be solubilized, a colloidal dispersion having increased viscosity is created. When the film-forming polymer has a molecular weight which is too large for a colloidal dispersion to be formed, the polymer agglomerates, creating an emulsion dispersion having a viscosity virtually identical to that of the solvent. Hence, the polymer-solvent system is either a macroscopially homogeneous, microscopically homogeneous solution or a macroscopically homogenous, microscopically heterogeneous dispersion.

The self-encapsulating polymer-containing solution comprises a film-forming polymer in a solvent in which the polymer is soluble, and the particle itself. Therefore, the polymer-containing solution exists as a particle either dissolved or dispersed in the solvent-polymer phase. At times, a three-phase dispersion system can be used in which the carrier liquid constitutes the third phase. On a weight basis, for either a solution or a dispersion system, the total amount of polymer utilized based upon the total weight of the solution, formulation, etc., by total weight of the solution or formula, it is meant the total weight of all of the compound which makes up the self-encapsulating solution, dispersion, or formulation, including the particle, the core agent, the film-forming polymer, the liquid or solvent, and the like, ranges from about 0.1 percent to about 25 percent, with from about 2 to about 18 percent being desirable, and from 4 to 13 percent being preferred. Often times, instead of a single film-forming polymer, two or even three types of polymers including polymer dispersions can be utilized. As described below, the plurality of polymers may combine to unexpectedly control core system solubility in the wall system and the release characteristics therethrough. The amount of solvent ranges from about 35 percent to about 99 percent with from about 50 to about 90 being preferred. The amount of particle ranges from about 1 percent to about 40 percent with from about 5 to about 30 percent being preferred. Naturally, as will be better understood by referring to the examples in the specification, the various components or compounds can be varied to achieve specific changes in properties of the final product; that is, the encapsulated particle. Additionally, various adhesive agents, crosslinking agents, emulsifying agents, core agents, film-modifying polymers, and other additives may be added to further modify either the process or the end product properties.

Suitable polymers for use in the present invention relates to film-forming polymers which are capable of encapsulating the particle by coacervation and which form a polymeric film about the particle. Such a specific polymer is polyvinyl acetate having a weight average molecular weight range of from about 10,000 to about 100,000. Another suitable and desired polymer is selected from polyvinyl ethers wherein the repeating hydrocarbon group is an alkyl having from 2 to 10 carbon atoms, preferably 2 carbon atoms, and with the polymer having a weight average molecular weight of from about 10,000 to about 100,000. The polyvinyl ether and the polyvinyl acetate polymers dissolve in the solvent and characterize a solution with macroscopic and microscopic homogeneity.

Desirable polymers of the present invention relate to carboxylated acrylic polymers and copolymers such as those made from monomers having the formula $$H_2C=\underset{\underset{R_5}{|}}{C}-\underset{\underset{O}{\|}}{C}-OR_4$$

where $R_4$ is a hydrogen radical or a hydrocarbon group having from 1 to 30 carbon atoms and $R_5$ is a hydrogen radical or a hydrocarbon group having from 1 to 12 carbon atoms, both hydrocarbon groups selected from the class consisting of alkyl, cycloalkyl, aryl, and aralkyl. Desirably $R_4$ is an alkyl having from 1 to 4 carbon atoms and preferably is hydrogen. $R_5$, desirably, has from 1 to 3 carbon atoms and, preferably, either has 1 carbon atom or is hydrogen. By carboxylated, it is meant that a substantial number of the pendant groups of the polyacrylate contains carboxyl groups. Moreover, by copolymers, it is meant that the polymer may be made from 2 or more monomers having the above formulation. A preferred polymer is made from methacrylate monomers with a more preferred polymer being made from acrylic acid monomers.

Generally, any colloidal or emulsion-forming polymer can be utilized in the present invention where a dispersion; that is a colloidal or an emulsion dispersion, is desired. For example, various acrylic type polymers and interpolymers can be utilized. Other acrylic type polymers include the acrylic copolymer systems, acrylic-based polymer systems, acrylic aqueous colloidal dispersion resins, acrylic aqueous emulsion dispersion resins, and the like.

The molecular weight of the carboxylated acrylic polymers of the above formula, as well as the other acrylic type polymers generally determines the type of polymer-solvent-carrier system created. Generally, acrylic type polymers having a range from about 10,000 to about 400,000 solubilize into the solvents of this invention. Acrylic type polymers having a molecular weight range from about 400,000 to about 800,000 form a colloidal dispersion in the solvents of this invention. Acrylic type polymers having a molecular weight range from about 800,000 to about several million, e.g., 3 or 4 million, or greater form an emulsoidal dispersion in the solvents of this invention.

The colloidal and emulsoidal dispersions of acrylic type polymers are desirable for forming stronger films in situ during flight. When employed, these dispersion acrylic type polymers may comprise a lower concentration in the encapsulation blend than the solutions of acrylic polymers because the higher molecular weight material creates a stronger film when formed in situ.

Acrylic type polymers or copolymers having molecular weights greater than 400,000 are commercially available from Rohm & Haas Company under their trademark Rhoplex® and their trademark Acrysol™. Particular products found effective as film-forming emulsion polymers are Rhoplex® AC-64, Rhoplex® AC-22, Rhoplex® LC-45, Rhoplex® LC-40, Acrysol™ A-1, Acrysol™ A-3, and Acrysol™ A-5. Acrysol™ WS-12 provided effective film-forming as a colloidal dispersion.

It has been found that film-forming with dispersion polymers can also be effective at normal atmospheric temperature ranges.

With any film-forming polymer of the present invention, polymers with poor or negligible film-forming properties can be added to the solution or dispersion to modify the properties of the wall system. These polymers, in an amount of from about 0.1 to about 10 percent by weight, desirably from about 0.1 to about 5 percent by weight of the total solution or formulation, easily determinable by those skilled in the art, e.g., polyvinyl alcohol, polystyrene, and the like, become film-modifying polymers which, when combined with the film-forming polymers described above, unexpectedly alter core system solubility in the wall system, or control release characteristics of the wall system for the core system to release therethrough.

A highly preferred polymer compound of the present invention are the salts of interpolymers of alpha-beta olefinically unsaturated carbonyl monomers which contain N-methylol acrylic amides as set forth in U.S. Pat. No. 3,007,887, which is hereby fully incorporated by reference with regard to the preparation, content and description of the interpolymers. Generally, the interpolymer has the following structure:

where R and $R_1$ are members of the group consisting of hydrogen and methyl; $R_2$ is a member of the group consisting of methyl, ethyl, propyl and butyl; $R_3$ is a member of the group consisting of methyl and ethyl; n represents from 3 to 12 weight percent based on the combined weight of n, x, y and z; x represents from 8 to 25 weight percent based on the combined weight of n, x, y and z; y represents from 45 to 89 weight percent based on the combined weight of n, x, y and z; z represents from 0 to 44 weight percent based on the combined weight of n, x, y and z; the sum of the numerical value of $n+x+y+z$ is always exactly 100 and the groups n, x, y and z are present in a heterogeneous relative position. The interpolymer is converted from an alcohol solution to water solutions by the addition of water having neutralizing agents such as ammonia, a hydrazine, or a low-boiling amine to the alcoholic solution of the interpolymer followed by an azeotropic distillation which removes the last traces of the alcohol and the excess neutralizing agent. The final aqueous solution of the polymer salt is preferably in the range of pH 5–8 and more preferably in the range of pH 6–7 with a total solids content of from about 2 to 40 percent by weight and preferably from about 5 to about 30 percent by weight of polymer in water.

The interpolymers embodied in this invention are those compositions comprising from 45 to 89 parts by weight of a lower methacrylic acid ester, from 0 to 44 parts by weight of a lower methacrylic acid ester, from 3 to 12 parts by weight of an alpha-beta olefinically unsaturated carboxylic acid having a terminal $CH_2=C<$group and having from 3 to 4 carbon atoms and from 8 to 25 parts by weight of an N-methylol alpha-beta olefinically unsaturated carboxylic acid amide having a terminal $CH_2=C<$group and having from 4 to 5 carbon atoms.

The lower acrylic acid esters useful in this invention include those in which $R_2$ in the above formula is an aliphatic hydrocarbon group having from 1 to 4 carbon atoms such as methyl acrylate, ethyl acrylate, n-propyl acrylate, isopropyl acrylate, n-butyl acrylate, isobutyl acrylate and secondary butyl acrylate. The most preferred lower acrylic acid esters are methyl acrylate and ethyl acrylate. The lower acrylate acid esters are useful in the range of from about 45 to about 89 weight percent based on the weight of the other monomers.

The lower methacrylic acid esters useful in this invention include those in which $R_3$ in the above formula is an aliphatic hydrocarbon group having from 1 to 2 carbon atoms such as methyl methacrylate and ethyl methacrylate. The preferred methacrylic acid ester is methyl methacrylate. The lower methacrylic acid esters are useful in the range of from about 0 to about 44 weight percent based on the weight of the other monomers.

The alpha-beta olefinically unsaturated carboxylic acids embodied in this invention include acrylic acid and methacrylic acid. The alpha-beta olefinically unsaturated carboxylic acids are useful in the range of from about 3 to about 12 weight percent based on the weight of the other monomers.

The N-methylol acrylic amides embodied in this invention include N-methylol acrylamide and N-methylol methacrylamide. The most preferred N-methylol acrylic amide is N-methylol acrylamide. The N-methylol acrylic amides are useful in the range of from about 8 to about 25 weight percent based on the weight of the other monomers.

The weight average molecular weight of the polymer represented by the above interpolymer structure generally ranges from about 20,000 to about 1,000,000 with a weight of from about 30,000 to about 250,000 being preferred.

In the molecular weight range between 300,000 and 500,000, the interpolymer structure forms a colloidal dispersion in the solvents of the present invention. In the molecular weight range greater than about 500,000 to about 2 or 3 million, the interpolymer structure forms an emulsoidal dispersion in the solvents of the present invention. Thus, the interpolymers constitute yet another type of polymers which form polymeric dispersions.

Specific examples of the above interpolymers include Carboset XL11 (molecular weight of about 45,000), Carboset 514 (molecular weight of about 30,000), Carboset 515 (molecular weight of about 70,000), Carboset 525 (molecular weight of about 260,000), Carboset 526 (molecular weight of 300,000), all manufactured by The B. F. Goodrich Company.

The solvent or carrier liquid may be any liquid which will solubilize or colloidally or emulsoidally disperse the above polymers. Generally, water and alkanols having from 1 to 5 carbon atoms, and combinations thereof, may be utilized. Examples of specific alcohols include methanol, propanol, isopropanol, butanol, isobutanol, pentanol, etc., with ethanol being preferred. Other suitable solvents includes acetone, diisobutyl ketone, methyl ethyl ketone, dioxane, and methylene chloride. Moreover, other solvents may be used in which the particle is generally soluble or dispersible therein. In the dispersion system, all of the above examples are possible with methanol and water being desirable carrier liquids. Water is the preferred dispersing liquid for colloidal and emulsion dispersion polymer systems.

The particle can be a solid. However, in most instances, the particle is a liquid. Regardless of whether the particle is a solid or a liquid, it can be any compound which, as part of the self-encapsulating solution or mixture, can be ejected or sprayed by either known or conventional ejecting or spraying apparatus. Although the particles may be of any size so long as they can be sprayed or ejected by an apparatus, they are desirably small to facilitate in the ease of ejecting or spraying the solution or, generally, due to their nature of application. For example, at least 90 percent of the particles having a size ranging from less than 1 micron to 300 microns may be utilized, although, generally, they are from a much smaller range as from about 1 to about 150 microns. For insecticides, odorants, etc., the application of particles smaller than 100 microns, as from 1 to 50 microns, are often preferred. The smaller particle sizes permit a thinner wall construction formed by the polymer in situ during flight. Therefore, the concentration of the film-forming polymer may be reduced in the overall encapsulation recipe. However, the higher molecular weight polymers, which are colloidally or emulsoidally dispersed in the solvent, at concentrations of 0.01 percent may form strong films for particles having a size less than 100 microns.

Naturally, it is desirable that the particle, the solvent, or carrier liquid, and the polymer(s) be compatible with each other in that they lack chemical interaction.

The particle compounds include nutrients such as fertilizers or vital trace minerals, insecticides, acaricides, nematicides, molluscicides, herbicides, fungicides, pheromones, odorants, fragrances, attractants, repellents, and innocuous materials for scientific effort, keyed to spray equipment design, spray effects depending upon environmental influences, and the like, or other materials where rapid and controlled delivery to a given target is desired. Specific examples of these classes of particles are set forth below.

| Trace Nutrients | |
|---|---|
| Zinc chloride | Boric acid |
| Zinc sulfate | Sodium borate |
| Ferric chloride | Sodium selenate |
| Ferric sulfate | Cobalt sulfate |
| Copper sulfate | Sodium molybdate |
| Copper oxychloride | Manganese chloride |
| Manganese sulfate | |

INSECTICIDES AND ACARICIDES

O,O-diethyl-O-p-nitrophenyl phosphorothioate (parathion)

O,O-dimethyl-O-p-nitrophenyl phosphorothioate (Methyl parathion)

O,O-dimethyl-O-(3-methyl-4-nitrophenyl)phosphorothioate (Sumithion)

O,O-diethyl-O-(2-isopropyl-6-methyl-5-pyrimidinyl) phosphorothioate (Diazinon)

O,O-dimethyl-O-(3-methyl-4-(methylthio)phenyl) phosphorothioate (Fenthion)

Pyrethrin-piperonyl butoxide and pyrethroids, with or without synergists or adjuvants 1-naphthyl methylcarbamate (Carbaryl)

2-(1-methylethoxy)phenol methylcarbamate (Baygon, manufactured by Chemagro)

2-methyl-2-(methylthio)propionaldehyde-O-(methyl carbamoyl)oxime (Aldicarb, manufactured by Union Carbide)

S-methyl-N-[methylcarbamoyl(oxy)] thioacetamide (lannate)
Chlorinated camphene, 67 percent Octachlorocamphene (Toxaphene, manufactured by Hercules)
Tricalcium arsenate
Sodium aluminum fluoride
Dichlorodiphenyltrichloroethane
Tricyclohexyltin hydroxide (Plictran, manufactured by Dow Chemical)
1,1,1-Trichloro-2,2-Bis(P-methoxyphenyl)ethane(methoxychlor)
1,2-dibromo-2,2-dichloroethyl dimethyl phosphate (naled)

NEMATICIDES

O,O-diethyl-O-2,4-dichlorophenyl phosphorothioate (dichlorofenthion)
N,N-dimethyl dodecanamide
O-Ethyl S,s-dipropyl phosphorodithioate (Ethoprop)

MOLLUSCICIDES

Copper sulfate
Tributyltin fluoride
n-tritylmorpholine(trifenmorph)
Sodium pentachlorophenate
Niclosamide

HERBICIDES 2,4-dichlorophenoxyacetic acid (2,4-D)
Alkylamine salts of 2,4-D
Butoxyethanol ester of 2,4-D
2,4,5-trichlorophenoxyacetic acid (2,4,5-T)
2-(2,4,5-trichlorophenoxy)propionic acid (Silvex)
3-amino-2,5-dichlorobenzoic acid (chloramben)
3,6-dichloro-o-anisic acid (Dicamba)
2,3,6-trichlorophenylacetic acid (Fenac)
2,6-dichlorobenzonitrile (Dichlobenil)
N,N-diallyl-2-chloroacetamide (Randox)
S-Ethyl diisobutylthiocarbamate (Sutan)
Isopropyl N-(3-chlorophenyl)carbamate (chloropropham)
3-amino-1,2,4-triazole (Amitrole)
2-chloro-4,6-Bis(ethylamino)-S-triazine (Simazine)
2-chloro-4-ethylamino-6-isopropylamino-S-triazine (Atrazine)
6,7-dihydrodipyrido(1,2-a:2',1'-c)pyrazinediium dibromide (Diquat)

FUNGICIDES

Hexachloraphene
Triphenyltin acetate
Methyl-1-(butacarbamoyl)-2-benzimidazole carbamate (Benomyl)

PHEROMONES

Disparlure; cis-7,8-epoxy-2-methyloctadecane
Gossyplure; a mixture of 2,2-7,11-hexadecadienyl acetate and 2,E-7,11-hexadecadienyl acetate
Looplure; (2)-7-dodecenyl acetate

PLANT REGULANTS

Maleic hydroxide (Ethrel)
Glycosate (Round Up)
Triacontinol

When pheromones are used as the particle or core material, the amount thereof by weight ranges from about 0.01 percent to about 40 percent, with from about 0.05 to about 10 percent being preferred. Usually, the pheromone is contained with a core agent such as soy oil, a fatty acid, and the like. The pheromones may be of a volatile nature.

The self-encapsulating polymer-containing solution of the present invention is applied by ejecting or spraying a liquid solution, colloidal dispersion or emulsion dispersion from known or conventional spray equipment. Such spray equipment can be affixed to any suitable vehicle such as an aircraft, truck, a spray system in a field, and the like, utilizing techniques and artifices common to the particular art, for example, as in the agricultural and public health areas. Subsequently and immediately after ejection, the spray during flight through the intervening atmosphere rapidly loses solvent via evaporation, coacervation occurs, and small solid spheres are formed having generally a very uniform shape and size. Thus, in-flight encapsulation occurs during the short passage between the egress of a spray of ejection apparatus and a target area with the delivered encapsulated product being a solid. Each sphere or microcapsule is comprised of an outer enveloping polymeric membrane or wall system and an inner core of the particle or an agglomeration of particles or core system. The encapsulated product can be delivered to and within the target area using narrow spectrum sprays (for example, that produced by the Beeco Mist Nozzle, designed to provide a sufficient transport of the active ingredient to its target area). Generally, the various spray systems can be adjusted such that a few ounces of the composition or solution is utilized for each acre or up to about 2 to 5 gallons of solution per acre. In the latter case, water is generally utilized as a solvent.

Moreover, applicants' composition, solution and process, aided by the film-forming polymer coating of a particle or particles, can result in fairly uniform-sized encapsulated products, that is, encapsulated products in which at least 90 percent of the products fall within a narrow range, and as set forth hereinabove. Of course, the size of the encapsulate products can be varied by changing the proportion of the various ingredients, the amount of crosslinking agent, core agent and the like, as set forth hereinbelow as well as utilizing different spray equipment, particularly the nozzles thereon which largely determine the initial egress droplet size spectrum. Thus, encapsulated products having a particle size of from 1 micron to 500 microns or larger can be produced. Generally, however, encapsulated products of from 1 to about 150 microns are desired for many applications. A specific example of a suitable spraying apparatus which delivers droplets over a narrow range is manufactured by the Beeco Products Corporation. As a rough rule of thumb, the encapsulated particle size will be 80 percent of the initial droplet size leaving a spray or ejecting apparatus, when the amount of solvent is equal to the amount of particles on a weight basis. Since great uniformity and droplet size as well as the encapsulated product can be controlled as described herein, the microcapsules of the present invention are ideal as a research tool for the study and evaluation of spray equipment and effects of atmospheric parameters upon the spraying art.

Additionally, micro-encapsulated products of the present invention result in a controlled leaching rate of the particular particle at the site of application or target area so that the particle availability is greatly prolonged and leads to greater efficacy, reduced contamination, and economic benefit. Also, non-persistent agents can be encapsulated and essentially rendered persistent at the microcapsule application site, so that once released in the environment, it becomes subject to natural degradation factors so that persistency is low at the site of application; again a positive contribution to enhance environmental quality.

In addition to varying the components of the system, additional compounds or agents may be added to the solution to control various parameters or functions such as capsule size, the enveloping polymeric membrane thickness, the leaching rate, the rate of evaporation, the emitted droplet size, adhesion, particle bulk, particle volatility, and particle solubility and the like. Naturally, such additives should not have any deleterious chemical interaction with any of the components of the system.

In those circumstances where the particle is an active ingredient requiring minute concentrations over large surface areas, additional core agents insoluble in the film-forming polymer may add bulk to the material within the core inside the film wall. Otherwise, the minute concentration of particle may become trapped within the polymer film wall, causing uncontrolled release.

Whenever a particle is particularly volatile, controlled release is necessary to provide effective and efficient use of the particle in the environment. Pheromones are particularly volatile, and a core agent controls its release.

Whenever a particle has a degree of solubility with the film-forming polymer, a core agent may become necessary to decrease the particle solubility in the polymer. This addition of a core agent is particularly effective for particles which are either solubilized in solvents, miscible with the film-forming polymer, or may be slightly soluble in the polymer. Methyl parathion and m-diethyltoluamide (DEET) are effectively restrained within the core of the encapsulation with the addition of a core agent.

The mechanisms of coacervation, encapsulation, and controlled release are enhanced by a separation of the in situ product into a film-forming polymer wall and a particle liquid or solid core. This separation is enhanced greatly by the use of core agents. Further, a core agent may serve to prevent degradation of the agent or encapsulant from ultra-violet radiation.

Core agents are selected from any of the following groups of compounds:

1. Monohydric alcohols having from 6 to 20 carbon atoms and the mono- and polyunsaturated derivatives thereof; e.g., octyl alcohol, decyl alcohol, dodecyl alcohol, etc.

2. Polyhydric alcohols having from 2-10 carbon atoms and the monoesters thereof, diesters thereof, triesters thereof, monoethers thereof; homopolymers thereof, and the homopolymer monoethers thereof; e.g., glycol and polyglycol monoethers, polypropylene glycol monobutyl ether, propylene glycol, polypropylene glycol, polyethylene glycol, etc.

3. Saturated and unsaturated fatty acids having from 8-20 carbon atoms and the alkyl esters thereof; e.g., monoglycerides, diglycerides, triglycerides, glycerine, etc.

4. Absorbant or porous solids including carbon black, silica, and molecular sieves, and combinations thereof;

5. Sunscreen materials; and

6. Soy oil.

Of the core agents, desirable compounds are the polyhydric alcohols and the fatty acids. Preferably, the di- and triesters of the polyhydric alcohols and especially the triglycerides serve as effective core agents.

The core agent may be added to the solution or dispersion at a range from about 1 to about 40 percent by weight, and desirably at a range from 2 to about 25 percent by weight of the total weight of the solution or formulation. The preferred range is from 3 to 5 percent.

Generally, the enveloping polymer membrane of the polymers of the present invention are degraded in the environment. The effects of the rain and sun can be detrimental to the longevity of the particle and the active ingredients in the core. However, longevity can be enhanced in several ways as by increasing the amount or thickness of the enveloping polymer membrane. This can be achieved by utilizing a greater ratio of polymer. Moreover, longevity can be increased by utilizing specific types of polymers such as various specific interpolymers which show improved leaching rates over similar polymers. Crosslinking agents may also be added to the solution so that, upon encapsulation, the polymeric membrane is crosslinked. Crosslinking decreases the pore size and, hence, increases duration or longevity so that the final particle may be utilized over a period of several months. Suitable crosslinking agents include urea, and other triamines, diamines, triamides and diamides, as well as the alkaline earth metal salts wherein the alkaline earth is beryllium, magnesium, barium or, preferably, calcium. Suitable anions include carbonate, bicarbonate, nitrate, oxide, hydroxide, and the various halogens, for example, $F^-$, $Cl^-$, $I^-$, and $Br^-$. Of these, the calcium salts, especially calcium hydroxide, are desirable and calcium chloride is preferred. Moreover, the interpolymers may be crosslinked with zinc oxide as taught in U.S. Pat. No. 3,749,772. Generally, the extent of the crosslinking agent may range from about 0.01 to about 0.5 percent by weight based upon the total weight of the solution with the range of from about 0.05 to about 0.25 being preferred. Naturally, the crosslinking agents should be non-toxic, generally, non-reactive with the components, and soluble in the solvents of the present invention.

Other modifications to the wall system which affects longevity of the wall include the addition of film-modifying polymers described above. These secondary polymers may be joined by other emulsion or dispersion materials to control wall thickness and pore size. Additionally, sunscreen materials which have been itemized as core agents may also be added to the wall system for encapsulant longevity.

The self-encapsulating polymer-containing solution of the present invention, generally, must be maintained in relatively a non-acidic state, usually at a pH of 6.5, and preferably 7.0, to 8.0, to prevent crosslinking prior to solvent evaporation. Typical alkaline agents may be utilized to achieve such a pH range, such as ammonia, sodium hydroxide, and the like. Normally, only very small amounts are required as on the range of 0.01 to about 50 percent by weight of the total solution or mixture.

In many applications, especially those involving the delivery of insecticides to protect crops and the like, long term adhesion of the microcapsule to foliage or other plant structures is desired. The amount by weight of adhesive agent ranges from about 0.1 to about 10 percent, and desirably from about 0.1 to 3 percent, based upon the total weight of the solution. Improved adhesion can be obtained by generally utilizing the lower molecular weight interpolymers and/or adhesive agents such as alkyl esters. The alkyl esters are of the formula $$R_6-\overset{O}{\underset{\|}{C}}-O-R_7$$

where $R_6$ and $R_7$ contain from 2 to 5 carbon atoms. Ethyl acetate is the preferred alkyl ester. Generally, any conventional adhesive agent which improves adhesion of the encapsulated particle to the plant, etc.; that is, the earth target, biota, etc., can be utilized. Thus, the diesters of phthalic acid, e.g., di-octylphthalate can be used. Other compounds which serve as adhesive agents include wall softening agents such as some of the film modifying polymers, e.g., polyvinyl alcohol.

The effect of the various ingredients upon the membrane thickness, adhesion, longevity of release and the like will be better understood by reference to Table I which sets forth formulations in Examples 1 through 12. In Example 1, the interpolymer utilized was 16 percent of a high molecular type such as Carboset 525, 50 percent by weight of alcohol, and 34 percent by weight of the particle. In Example 1, the particle was actually in solution as a 50—50 mixture of benzoic acid and orthotoluic acid. This example, as well as the other examples were sprayed through a Beeco Mist spray gun utilizing a 60-micron pore size nozzle. The polymer film totally encapsulated the crystallized acids used as a particle and the encapsulated product were spheres. Example 2 illustrates a crosslinked version of Example 1 wherein calcium chloride was used as a crosslinking agent along with a small amount of ammonia to prevent premature crosslinking prior to solvent evaporation. The thickness of the polymer membrane or wall system was greater than that of Example 1. Decreasing the average molecular weight of the polymer component as in Example 3 decreases the membrane or wall thickness and, thus, lowers the field life of the capsule. For long life, that is from about 3 to 6 months, the polymer of Example 4 may be crosslinked as shown in Example 5.

As previously noted, the use of low molecular weight polymers provide some degree of tackiness so that the encapsulated product will adhere to leaves, stems, and the like. However, since lower molecular weight polymers are often deleterious to film-forming properties, increased adhesion time of several weeks and even several months can be obtained by adding small amounts of ethyl acetate or butyl cellosolve, as set forth in the formulation of Example 6. The process of adhesion promotion is as follows. Utilizing the formulation of Example 7, the microcapsule forms and crosslinking occurs, and as soon as the alcohol and ammonia evaporate, the process progressing in a few seconds after the egress from a spraying apparatus, depending upon the droplet surface area and volatility of the solvent. However, the ethyl acetate or butyl cellosolve is occluded by the forming envelope and, thus, for the most part, is present at the time of foliage contact. At the instant of such contact and for several seconds thereafter, the ethyl acetate moves from the microcapsule, penetrating the outermost dermis of the plant. This process, mainly a desorption phenomenon, results in a slight flow of the polymer envelope into the foliage structure, thus enhancing adhesion. The process is rapid and relies on a quantity of an adhesive aid, such as ethyl acetate. Moreover, no damage to agricultural important plants arises from momentary contact with the ethyl acetate.

Water systems and water/alcohol systems have also been utilized as where the uses of a diluted alcohol would be advantageous. Examples 8 and 9 illustrate such systems, based upon a water soluble interpolymer, particularly, Carboset XLII. In Example 8, a water system is utilized and, hence, the particles are limited to water soluble and dispersible compounds. Although this formulation is of poor environmental resistance, it is used in delivering trace nutrients such as water soluble zinc, copper, iron, and other salts. The formulations of Examples 8 and 9 result in capsule formation during flight, but due to the amount of $H_2O$ present at the time of impact, the effects may be a soft capsule that flows to meet the contour of the impingement surface. Rigid spheres are usually not formed. Such systems may also be crosslinked and adhesion promoted. In contrast, the porosity of a microcapsule may be enhanced by the utilization of an alcohol insoluble with a water soluble additive such as calcium benzoate, calcium hydroxide, and calcium carbonate. Considering Example 10, during in-flight encapsulation, most of the calcium chloride is trapped within a polymer membrane. However, once the crosslinked capsule has adhered to a given surface and comes into contact with water, the porosigen, calcium benzoate, is rapidly lost through leaching and a pore structure remains allowing water penetration of the core particle. The calcium hydroxide is used as in Example 11; it not only serves to crosslink the polymer but also imparts alkalinity and, thus, no ammonia is necessary. Since calcium hydroxide is alcohol soluble, a considerable fraction is found in the core area. However, sufficient quantities exist within the polymer envelope to enhance the growth of porosity.

TABLE I

| | RECIPE |||||||||||| 
| | EXAMPLE |||||||||||| 
| INGREDIENT | 1 | 2 | 3 | 4 | 5 | 6 | 7 | 8 | 9 | 10 | 11 | 12 |
|---|---|---|---|---|---|---|---|---|---|---|---|---|
| Carboset 525 | 16% | 16% | 8% | 6% | 6% | 6% | 6% | — | — | 12% | 11% | 12% |
| Carboset 526 | — | — | — | 7% | 7% | — | — | — | — | — | — | — |
| Carboset XL11 | — | — | 8% | — | — | — | — | 4% | 6.25% | 12% | 12% | 10% |
| Carboset 514 | — | — | — | — | — | 6% | 6% | — | — | — | — | — |
| Ethanol | 50% | 50% | 50% | 69% | 69% | 66% | 66% | — | — | 37.85% | 27% | 44% |
| Water | — | — | — | — | — | — | — | 89.75% | 87.5% | 7% | 15% | — |
| Ethyl Acetate | — | — | — | — | — | 1% | 1% | — | — | — | — | — |
| Calcium Chloride | — | 0.1% | — | — | 0.2% | — | 0.2% | — | — | 0.1% | — | — |
| Ammonia | — | 0.05% | — | — | 0.1% | — | 0.1% | — | — | 0.05% | — | — |
| Calcium Benzoate | — | — | — | — | — | — | — | — | — | 1% | — | — |
| Calcium Hydroxide | — | — | — | — | — | — | — | — | — | — | 2% | — |
| Lauric Acid | — | — | — | — | — | — | — | — | — | — | — | 3% |
| Agent | 34% | 33.85% | 33% | 18% | 17.7% | 21% | 20.7% | 6.25% | 6.25% | 30% | 32% | 31% |

The invention will be better understood by reference to the following additional examples.

EXAMPLE A

Figure 1:
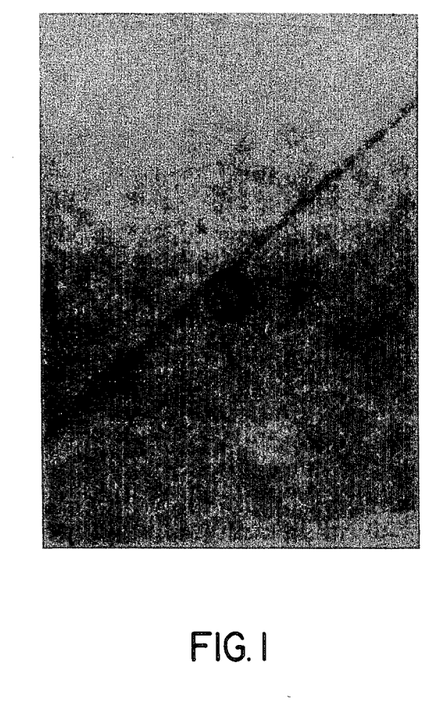
FIG. 1 is a photograph of an encapsulated particle, according to the present invention, wherein a polymeric film is shown about the particle and the film is adhered to a glass strand.
Figure 2:
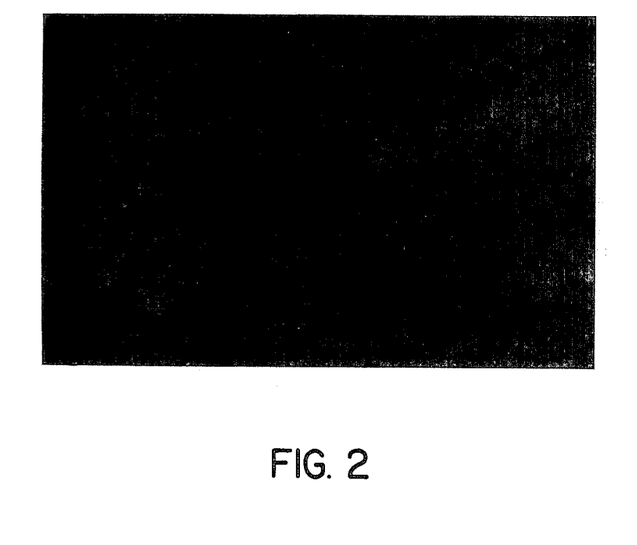
FIG. 2 is a photograph similar to FIG. 1 wherein the encapsulated particle is adhered to the junction of two glass strands.
Figure 3:
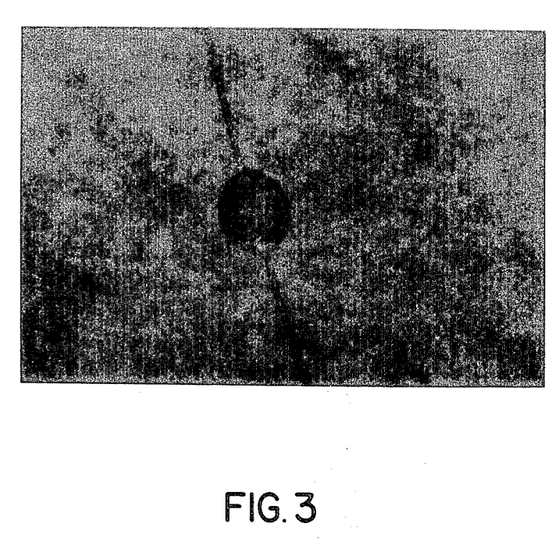
FIG. 3 is another photograph showing a particle polymerically encapsulated about a glass strand.
Figure 4:
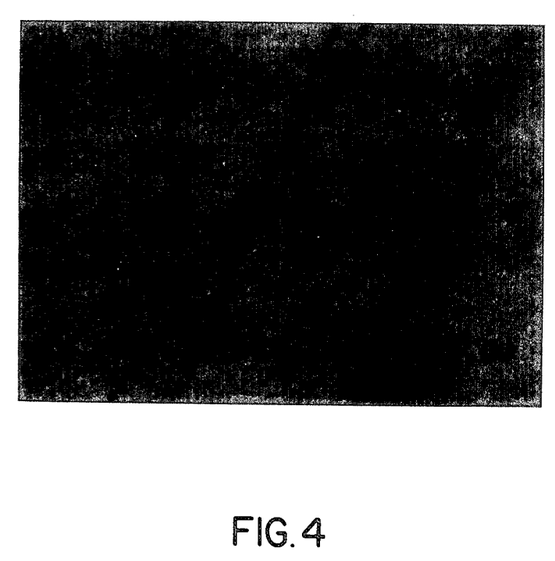
FIG. 4 is another photograph showing an encapsulated particle attached to the intersection of two glass strands.

A solution containing 75 parts by weight of pyrethrin-piperonyl butoxide, 25 parts by weight of Carboset 525, and 100 parts by weight of ethanol was made. The solution was mixed and added to a manual spray ejector such as a hand-operated atomizing pump. The solution was sprayed in the direction of glass fibers located approximately 1 to 2 feet away from the egress of the spray pump. Upon spraying, the Carboset encapsulated the pyrethrin-piperonyl butoxide. The graphic analysis, as shown in photographs 1 through 4, clearly depicts the polymeric film formed about the pyrethrin-piperonyl butoxide particle. The glass strands in all photographs are 10 microns in diameter. As apparent from the photographs, FIG. 1 definitely shows a polymer formed about the particle, with the polymer adhered to a glass strand. In FIG. 2, the polymer is formed about the intersection of two strands with another encapsulated particle located about a single strand. FIG. 3 discloses the encapsulated film being located about the liquid particle. In this photograph, the film actually formed completely about a portion of a glass strand. FIG. 4 is similar to FIG. 2 in that it reveals a polymeric film formed about the intersection of two glass strands with a liquid particle being located therein.

EXAMPLE B

Thirty parts by weight of Carboset XL11 having a molecular weight of approximately 45,000 in a 30 percent aqueous dispersion was mixed with 100 parts of water. To this was added 120 parts of Dursban containing 75 percent of an active ingredient of O,O-diethyl-O-3,5,6-trichloropyridinylthionophosphate. These ingredients were mixed and the solution had a pH of 6.7. Utilizing a hand spray pump, the solution was sprayed towards a target area. Photographs reveal that the active ingredient was fully encapsulated by the particle.

Use of acrylic polymers in a dispersion system is explained by referring to Examples C, D, and E.

EXAMPLE C

The following acrylic dispersions were tested for their potentials in the encapsulation of particles. These polymer dispersions were products of the Rohm and Haas Co. (Philadelphia). Soy oil was the particle.

TABLE II

| R. Dispersion | MFFT (°C.)* | Glass Transition Temperature ($T_g$) °C. |
|---|---|---|
| AC-64 | 5-9 | 13 |
| LC-40 | 2 | −9 |
| LC-45 | 2 | −10 |
| LC-67 | 0 | −45 |

*Minimum Film Formation Temperature

The LC series of dispersions are characterized by softness and adhesion, with LC-67 being internally plasticized. The AC-64 is harder in comparison.

Soybean oil (50 parts) was emulsified with Tween 80 (1.5 parts) and water (100 parts). The Rhoplex dispersions were made up to either 30 or 50 parts of polymer in 200 parts water. The two emulsions were mixed, diluted to spray volume (500–1,000 ml) with water.

The solutions were tested as follows: the emulsion was sprayed through a Mini Ulva sprayer whose $D_{max}$ was in the range of 125 microns. The spray cloud was impinged after the flight process on (1) paper, (2) teflon-coated slides, (3) glass slides (1×3 inch) and on the target for use in the Scanning Electron Microscope. The effective nature of the encapsulated droplets were evaluated by their SEM results. In this series of tests the AC-64, LC-45 and LC-40 dispersions gave excellent microcapsules at 30 and 50 percent wall dispersion concentration. The LC-67 was tested only at 50 percent wall content and gave less desirable results relative to capsule form and stability.

EXAMPLE D

A suspension-solution of the ammonium salt of Carboset®525 and Rhoplex®AC-64 was made by dissolving 5 parts of Carboset 525 ammonium salt in 100 parts water and adding 5 parts of 60 percent AC-64dispersion. Ninety parts of soybean oil was emulsified with 3 parts of Tween 80 in 500 parts of water. The two emulsion-suspension-dispersion-solutions were mixed and sprayed as in the previous example. Excellent microcapsules with approximately 10 percent wall were formed as proven by light microscope inspection and by SEM pictures.

EXAMPLE E

One hundred parts of N,N-diethyl-meta-toluamide (DEET) repellent, were emulsified in 200 parts of water and added to 200 parts of water containing 40 parts of AC-64 (60 percent active). Addition of 5 parts Automate Red dye to the emulsified core liquid allows simplified light microscopy evaluation. The emulsion-dispersion was diluted to 500 ml with water and sprayed as in the previous examples. Excellent microcapsules of DEET were formed which controlled the release of the DEET over a 10–15 day period, when tested by spraying in a horse barn. On horses, flies, including horn flies were repelled for 3–5 day periods.

Use of various core agents is explained by referring to Examples F, G, and H.

EXAMPLE F

One hundred parts of N,N-diethyl-meta-toluamide (DEET) repellent were added to 10 parts of soybean oil in 200 parts acetone. The soybean oil acted as a core agent for solubility control in limiting the solubility of the DEET core liquid in Carboset 525 polymer and in controlling the volatility of the DEET. The DEET-soybean oil core system was added to 300 parts acetone containing 20 parts of Carboset 525. The solution was sprayed out as in the previous example to give excellent microcapsules with adequate wall stability, and a well defined wall system-core system. In the absence of the core modifying agent, the Carboset 525 and the DEET are miscible.

EXAMPLE G

Glossyplure (pink bollworm pheromone) 2 (grams) parts were dissolved in 300 parts cotton seed oil containing 3 percent Tween 80 as an emulsifier. Three hundred parts of Carboset 525 in 600 parts methanol and 30 parts ammonium hydroxide was added to 1 gallon water. The core liquid was then added and the total emulsion volume made up to 2 gallons. A total of ten acres of irrigated cotton was sprayed at the rate of 2 gallons of the above mixture per acre. Pink bollworm mating was substantially totally interrupted for a period of 20 days as evidenced by the absence of trap catches of male moths in pheromone-baited traps in the cotton field.

The core modifier (cottonseed oil) acts to allow excellent microcapsule formation and to limit the volatility of the pheromone (Gossyplure) over the twenty-day period. In laboratory type tests, oleyl alcohol, hexadecanol and decanol have been proven to be effective core modifiers, for various pheromones including Indian Meal Moth pheromone which remained actively emitted from microcapsules on foliage for periods up to 40 days, as measured by male activity towards air streams blown over microcapsules on leaves in a glass bioassay system.

EXAMPLE H

Rhoplex AC 64, 10 parts, was added to 100 parts water containing 5 parts of polystyrene dispersion. The polystyrene acted as a core-wall modifier. Soybean oil (20 parts) was emulsified in 100 parts water and added to the Rhoplex AC 64-polystyrene dispersion. The dispersion was diluted to 300 ml and sprayed as described previously. Stable microcapsules with well defined wall system-core system core characteristics were formed.

The Rhoplex emulsion dispersions act in the presence of core liquids which allow capsule wall formation. Dioctyl phthalate and DEET are examples of Rhoplex polymer emulsion modifiers which assist in wall formation.

While having described the invention in accordance with the patent statutes, the invention is measured by the following claims.

What is claimed is:

1. A process for the in situ encapsulation of particles between a spraying apparatus and an earth target, comprising the steps of:

(a) preparing a self-encapsulating polymer-containing dispersion;

said dispersion comprising by weight from about 0.1 percent to about 25 percent of a film-forming polymer capable of encapsulating a particle by coacervation, from about 35 percent to about 99 percent of a liquid, said liquid being a compound which will disperse said polymer, and from about 1 percent to about 40 percent of particles, or from about 0.01 percent to about 40 percent when said particle is a pheromone, said particle being soluble or dispersible in said solvent;

in situ encapsulating said soluble or dispersible particle by:

spraying into the earth's atmosphere said dispersion containing said soluble or dispersible particle from a spray apparatus, and immediately thereafter;

evaporating said solvent in said earth's atmosphere and coacervating during the passage from said spraying apparatus to an earth target said polymer and said particle in said earth's atmosphere so that said polymer substantially encapsulates said particle; and concurrently and directly applying said encapsulated particle to an earth target.

2. A process according to claim 1, wherein said polymer having a molecular weight greater than 300,000 is selected from the group consisting of (a) an acrylic type polymer or copolymer comprising a polymer or copolymer made from monomers having the formula

where $R_4$ is hydrogen or an alkyl, cycloalkyl, aryl, aralkyl having from 1 to 30 carbon atoms and $R_5$ is hydrogen or an alkyl, cycloalkyl, aryl, aralkyl having from 1 to 12 carbon atoms;

(b) the salt of (1) an interpolymer having the structure

where R and $R_1$ are members of the group consisting of hydrogen and methyl; $R_2$ is a member of the group consisting of methyl, ethyl, propyl and butyl; $R_3$ is a member of the group consisting of methyl and ethyl; n represents from 3 to 12 weight percent based on the combined weight of n, x, y and z; x represents from 8 to 25 percent based on the combined weight of n, x, y and z; y represents from 45 to 89 weight percent based on the combined weight of n, x, y and z; z represents from 0 to 44 weight percent based on the combined weight of n, x, y and z; the sum of the numerical value of $n+x+y+z$ is always exactly 100 and the groups n, x, y and z are present in a heterogeneous relative position, and (2) a member of the group consisting of ammonia, hydrazine, a low boiling primary aliphatic amine and a low boiling secondary aliphatic amine, said salt being soluble in water in the pH range of from about 5 to 8; and (c) combinations thereof;

wherein said liquid is selected from the group consisting of alcohols having from 1 to 5 carbon atoms, acetone, diisobutyl ketone, methyl ethyl ketone, dioxane, methylene chloride, water, and combinations thereof.

3. A process according to claim 2, wherein said particle is selected from the group consisting of an insecticide, a fertilizer, a trace mineral, an acaricide, a nematicide, a molluscicide, a herbicide, a fungicide, a pheromone, an odorant, a fragrance, an attractant, a repellent, a plant regulant, and combinations thereof.

4. A process according to claim 3, wherein said trace mineral is selected from the group consisting of zinc chloride, zinc sulfate, ferric chloride, ferric sulfate, copper sulfate, copper oxychloride, boric acid, sodium borate, sodium selenate, cobalt sulfate, manganese sulfate, sodium molybdate, manganese chloride, and combinations thereof, wherein said Nematicide is selected from the group consisting of O,O-diethyl-O-2,4- dichlorophenyl phosphorodithioate; O-ethyl-S,S-dipropyl phosphorodithioate (Ethoprop), N,N-dimethyl dodecanamide, and combinations thereof, wherein said molluscicide is selected from the group consisting of copper sulfate, n-tritylmorpholine (trifenmorph), tributyltin fluoride, sodium pentachlorphenate, niclosamide, and combinations thereof, and wherein said fungicide is selected form the group consisting of triphenyltin acetate, methyl-1-9(butacarbamoyl)-2-benzimidazole carbamate (Benomyl), hexachloraphene, and combinations thereof.

5. A process according to claim 4, wherein the amount of said polymer ranges from about 4 percent to about 13 percent by weight, wherein the amount of said liquid ranges from about 50 percent to about 90 percent by weight, and wherein the amount of said particle ranges from about 5 percent to about 30 percent by weight, or from 0.05 percent to about 10 percent when said particle is a pheromone.

6. A process according to claim 3, wherein said particle is a herbicide, said herbicide selected from the group consisting of 2,4-dichlorophenoxyacetic acid (2,4-D), alkylamine salts of 2,4-D, butyoxyethanol ester of 2,4-D, 2,4,5-trichlorophenoxyacetic acid (2,4,5-T), 2-(2,4,5-trichlorophenoxy)propionic acid (Silvex), 3-amino-2,5-dichlorobenzoic acid (Chloramben), 3,6-dichloro-O-anisic acid (Dicamba), 2,3,5-trichlorophenylacetic acid (Fenac), 2,6-dichlorobenzonitrile (Dichlobenil), N,N-diallyl-2-chloroacetamine (Randox), S-ethyl diisobutyl-thiocarbamate (Sutan), isopropyl N-(3-chlorophenyl)-carbamate (chloropropham), 3-amino-1,2,4-triazole (Amitrole), 2-chloro-4,6-Bis(ethylamino)iso-propylamino-S-triazine (Atrazine), 6,7-dihy-drodipyrido(1,2-a; 2',1'-c)pyrazinediium dibromide (Diquat), and combinations thereof.

7. A process according to claim 6, wherein the amount of said polymer ranges from about 4 percent to about 13 percent by weight, wherein the amount of said liquid ranges from about 50 percent to about 90 percent by weight, and wherein the amount of said particle ranges from about 5 percent to about 30 percent by weight, or from 0.05 percent to about 10 percent when said particle is a pheromone.

8. A process according to claim 3, wherein said particle is an insecticide or an acaricide selected from the group consisting of O,O-diethyl-O-p-nitrophenyl phosphorothioate (parathion), O,O-dimethyl-O-p-nitrophenyl phosphorothioate (Methyl parathion), O,O-dimethyl-O-(3-methyl-4-nitrophenyl)phosphorothioate (Sumithion), O,O-diethyl-O-(2-isopropyl-6-methyl-5-pyrimidinyl) phosphorothioate (Diazinon), O,O-dimethyl-O-[3-methyl-4-(methylthio)phenyl]phosphorothioate (Fenthion), Pyrethrin-piperonyl butoxide, pythroids, 1-naphthyl methyl-carbamate (Carbaryl), 2-(1-methylethoxy)phenyl methylcarbamate (Baygon), 2-methyl-2-(methylthio)propionaldehyde-O-(methyl carbamonyl) oxime (Aldicarb), S-methyl-N-[methylcarbamonyl (oxy)]thioacetamine (lannate), chlorinated camphene, 67 percent octachlorocamphene (Toxaphene), tricalcium aresenate, sodium aluminum fluoride, Dichlorodiphenyltrichloroethane, tricyclohexyltin hydroxide (Plictran), 1,1,1-trichloro-2,2-Bis(p-methoxyphenyl)ethane (methoxychlor), 1,2-dibromo-2,2-dichloroethyl dimethyl phosphate (Naled), and combinations thereof.

9. A process according to claim 8, wherein the amount of said polymer ranges from about 4 percent to about 13 percent by weight, wherein the amount of said liquid ranges from about 50 percent to about 90 percent by weight, and wherein the amount of said particle ranges from about 5 percent to about 30 percent by weight, or from 0.05 percent to about 10 percent when said particle is a pheromone.

10. A process according to claim 1, 2, 3, 4, 6, 8, 5, 7, or 9, wherein said polymer has a molecular weight such that said polymer becomes a colloid or an emulsoid with said liquid, the molecular weight of said acrylic polymer ranging from about 400,000 to about 4,000,000, and the molecular weight of said interpolymer salt ranging from about 300,000 to about 3,000,000.

11. A process according to claim 10, including adding from about 1 percent to about 40 weight percent of a core agent, said core agent selected from the group consisting of (a) monohydric alcohols having from 6 to 20 carbon atoms and the mono and polyunsaturated derivatives thereof; (b) polyhydric alcohols having from 2 to 10 carbon atoms and the monoesters thereof, the diesters thereof, the triesters thereof, the monoethers thereof, the homopolymers thereof, and the homopolymer monoethers thereof; (c) saturated and unsaturated fatty acids having from 8 to 20 carbon atoms and the alkyl esters thereof; (d) absorbent solids selected from the group consisting of carbon black, silica, and molecular sieves; (e) ultraviolet screening materials; (f) soy oil; and (g) combinations thereof.

12. A process according to claim 10, further comprising adding crosslinking agents to said dispersion prior to ejection for reaction with said polymer, and adding an alkaline compound to said solution so that the pH of said solution ranges from about 6.5 to about 8.0, said crosslinking agent being an alkaline earth salt, urea, a diamine, a triamine, a triamide, or a diamide, said alkaline earth salt selected from the group consisting of calcium, barium, beryllium and magnesium, said anion portion of said salt selected from the group consisting of carbonate, bicarbonate, oxide, hydroxide, nitrate, $F^-$, $Cl^-$, $I^-$ and $Br^-$, the amount of said crosslinking agent ranging from about 0.01 to about 5 percent by weight based upon the total weight of said solution and the amount of said alkaline compound ranging from about 0.01 to about 0.01 percent by weight based upon the total weight of said solution.

13. A process according to claim 10 further comprising adding an adhesive agent so that upon the in situ formation of an encapsulated particle from said solution and the concurrent and direct application of said encapsulated particle to an inert target, said adhesive agent improves the tackiness of said encapsulated particle to said target; and adding a secondary polymer to said film-forming polymer in said dispersion so that said secondary polymer may modify film-forming properties of the film formed by said film-forming polymer.

14. An in situ self-encapsulating polymer-containing formulation for concurrent and direct application to an earth target, comprising a self-encapsulating polymer-containing dispersion; said dispersion comprising by weight from about 0.1 percent to about 25 percent of a film-forming polymer having a molecular weight greater than 300,000 and capable of encapsulating a particle by coacervation, from about 35 percent to about 99 percent of a liquid, and from about 1 percent to about 40 percent of a particle, or from about 0.01 to about 40 percent when said particle is a pheromone, said particle being soluble or dispersible in said solvent;

said liquid being a compound in which said polymer is dispersible.

15. A formulation according to claim 14, wherein said polymer is selected from the group consisting of (a) an acrylic type polymer or a copolymer comprising a polymer or copolymer made from monomers having the formula where $R_4$ is hydrogen or an alkyl, cycloalkyl, aryl, or aralkyl having from 1 to 30 carbon atoms and $R_5$ is hydrogen or an alkyl, cycloalkyl, aryl, or aralkyl having from 1 to 12 carbon atoms; (b) the salt of (1) an interpolymer having the structure wherein R and $R_1$ are members of the group consisting of hydrogen and methyl, $R_2$ is a member of the group consisting of methyl and ethyl; n represents from 3 to 12 weight percent based on the combined weight of n, x, y and z, x represents from 8 to 25 percent based on the combined weight of n, x, y and z; y represents from 45 to 89 weight percent based on the combined weight of n, x, y and z; z represents from 0 to 44 weight percent based on the combined weight of n, x, y and z; the sum of the numerical value of $n+x+y+z$ is always exactly 100 and the groups n, x, y and z are present in a heterogeneous relative position, and (2) a member of the group consisting of ammonia, hydrazine, a low boiling primary aliphatic amine and a low boiling secondary aliphatic amine, said salt being soluble in water in the pH range of from about 5 to 8; and (c) combinations thereof; and wherein said liquid is selected from the group consisting of alcohols having from 1 to 5 carbon atoms, acetone, diisobutyl ketone, methyl ethyl ketone, dioxane, methylene chloride, water, and combinations thereof.

16. A formulation according to claim 15, wherein said particle is selected from the group consisting of an insecticide, a fertilizer, a trace mineral, an acaricide, a nematicide, a molluscicide, a herbicide, a fungicide, a pheromone, an odorant, a fragrance, an attractant, a repellent, a plant regulant, and combinations thereof.

17. A formulation according to claim 16, wherein said trace mineral is selected form the group consisting of zinc chloride, zinc sulfate, ferric chloride, ferric sulfate, copper sulfate, copper oxychloride, boric acid, sodium borate, sodium selenate, cobalt sulfate, sodium molybdate, manganese sulfate, manganese chloride, and combinations thereof; wherein said insecticide and said acaricide is selected from the group consisting of O,O-diethyl-O-p-nitrophenyl phosphorothioate (Parathion), O,O-dimethyl-O-p-nitrophenyl phosphorothioate (Methyl parathion), O,O-dimethyl-O-(3-methyl-4-nitrophenyl)-phosphorothioate (Sumithion), O,O-diethyl-O-(2-isopropyl-6-methyl-5-pyrimidinyl) phosphorothioate (Diazinon), O,O-dimethyl-O-[3-methyl-4-(methylthio)-phenyl] phosphorothioate (Fenthion), Pyrethrin-piperonyl butoxide, pyrethroids, 1-naphthyl methylcarbamate (Carabaryl), 2-(1-methylethoxy)phenyl methylcarbamate (Baygon), 2-methyl-2-(methylthio) propionaldehyde-O-(methyl carbamonyl) oxime (Aldicarb), S-methyl N-[methylcarbamonyl(oxy)] thioacetamine (Iannate), chlorinated camphene, 67 percent octachlorocamphene (Toxaphene), tricalcium arsenate, sodium aluminum fluoride, Dichlorodiphenyltrichloroethane, tricyclohexyltin hydroxide (Plictran), and combinations thereof; wherein said Nematicide is selected from the group consisting of O,O-diethyl-O-2,4-dichlorophenyl phosphorothioate(dichlorofenthion), O-ethyl-S,S-dipropyl phosphorodithioate (Ethoprop), N,N-dimethyldodecanamide, and combinations thereof; wherein said molluscicide is selected from the group consisting of copper sulfate, n-tritylmorpholine (trifenmorph), tributyltin fluoride, sodium pentachlorophenate, niclosamide, and combinations thereof; wherein said herbicide is selected from the group consisting of 2,4-dichlorophenoxyacetic acid (2,4-D), alkylamine salts of 2,4-D, butoxyethanol ester of 2,4-D, 2,4,5-trichlorophenoxyacetic acid (2,4,5-T), 2-(2,4,5-trichlorophenoxy)priopionic acid (Silvex), 3-amino-2,5-dichlorobenzoic acid (chloramben), 3,6-dichloro-O-anisic acid (Dicamba), 2,3,5-trichlorophenylacetic acid (Fenac), 2,6-dichlorobenzonitril (Dichlobenil), N,N-diallyl-2-chloroacetamine (Randox), S-ethyl diisobutyl-thiocarbamate (Sutan), isopropyl N-(3-chlorophenyl) carbamate (chloropropham), 3-amino-1,2,4-triazole (Amitrole), 2-chloro-4,6-Bis(ethylamino)isopropylamino-S-triazine (Atrazine), 6,7-dihydrodipyrido(1,2-a; 2', 1'-c)pyrazinediium dibromide (Diquat), and combinations thereof; and wherein said fungicide is selected from the group consisting of triphenyltin acetate, methyl-1-(butacarbamoyl)-2-benzimidazole carbamate (Benomyl), hexachloraphene, and combinations thereof.

18. A formulation according to claim 17, wherein the amount of said polymer ranges from about 4 percent to about 13 percent by weight, wherein the amount of said liquid ranges from about 50 percent to about 90 percent by weight, and wherein the amount of said particle ranges from about 5 percent to about 30 percent by weight, or from about 0.05 percent to about 10 percent when said particle is a pheromone.

19. A formulation according to claim 14, 15, 16, 17, or 18, wherein said salt of said interpolymer has a molecular weight from about 300,000 to about 3,000,000, and wherein said acrylic polymer has a molecular weight of from about 400,000 to about 4,000,000.

20. A formulation according to claim 19, further comprising crosslinking agents for reaction with said polymer upon ejection and including an alkaline compound so that the pH of said solution ranges from about 6.5 to about 8.0, said crosslinking agent being an alkaline earth salt, a urea, diamines, triamines, diamides, or triamides, said alkaline earth salt selected from the group consisting of calcium, barium, beryllium and magnesium, said anion portion of said salt selected from the group consisting of carbonate, bicarbonate, oxide, hydroxide, nitrate, $F^-$, $Cl^-$, $I^-$, $Br^-$, the amount of said crosslinking agent ranging from about 0.01 to about 5 percent by weight based upon the total weight of said solution and the amount of said alkaline compound ranging from about 0.01 to about 1 percent by weight based upon the total weight of said formulation.

21. A formulation according to claim 19, further comprising an adhesive agent so that upon the in situ formation of an encapsulated particle from said solution and the concurrent and direct application of said encapsulated particle to an inert target, said adhesive agent improves the tackiness of said encapsulated particle to said target; and a secondary polymer to said film-forming polymer in said dispersion so that said secondary polymer may modify film-forming properties of the film formed by said film-forming polymer.

22. A formulation according to claim 19, including from about 1 percent to about 40 weight percent of a core agent for modifying the solubility, the ultraviolet degradation, and the volatility of said particle with said polymer upon encapsulation, said core agent selected from the group consisting of (a) monohydric alcohols having from 6 to 20 carbon atoms and the mono and polyunsaturated derivatives thereof; (b) polyhydric alcohols having from 2 to 10 carbon atoms and the monoesters thereof, the diesters thereof, the triesters thereof, the monoethers thereof, the homopolymers thereof, and the homopolymer monoethers thereof; (c) saturated and unsaturated fatty acids having from 8 to 20 carbon atoms and the alkyl esters thereof; (d) absorbent solids selected from the group consisting of carbon black, silica, and molecular sieves; (e) ultraviolet screening materials; (f) soy oil; and (g) combinations thereof.

23. An encapsulated particle having been in situ encapsulated and concurrently and directly adhered to an earth target, comprising:
a core system and a wall system, said wall system comprising a polymer film encapsulating said core system;
said core system comprising a particle and a core agent, and wherein said polymer is selected from the class consisting of (a) polyvinyl acetate; (b) a polyvinyl ether wherein said repeating unit has from 2 to 10 carbon atoms; (c) an acrylic polymer or a copolymer made from monomers having the formula where $R_4$ is hydrogen or an alkyl, cycloalkyl, aryl, or aralkyl having from 1 to 30 carbon atoms and $R_5$ is hydrogen or an alkyl, cycloalkyl, aryl, or aralkyl having from 1 to 12 carbon atoms; (d) the salt of (1) an interpolymer having the structure wherein R and $R_1$ are members of the group consisting of hydrogen and methyl; $R_2$ is a member of the group consisting of methyl, ethyl, propyl and butyl; $R_3$ is a member of the group consisting of methyl and ethyl; n represents from 3 to 12 weight percent based on the combined weight of n, x, y and z; x represents from 8 to 25 percent based on the combined weight of n, x, y and z; y represents from 45 to 89 weight percent based on the combined weight of n, x, y and z; z represents from 0 to 44 weight percent based on the combined weight of n, x, y and z; the sum of the numerical value of $n+x+y+z$ is always exactly 100 and the groups n, x, y and z are present in a heterogeneous relative position, and (2) a member of the group consisting of ammonia hydrazine, a low boiling primary aliphatic amine and a low boiling secondary aliphatic amine, said salt being soluble in water in the pH range of from about 5 to 8 and (e) combinations thereof;
said core system having been in situ encapsulated by said wall system and concurrently and directly applied to the earth target; and
wherein said core agent modifies the solubility, the ultraviolet degradation, and the volatility of said particle upon encapsulation into said core system, said core agent selected from the group consisting of (a) monohydric alcohols having from 6 to 20 carbo atoms and the mono- and polyunsaturated derivatives thereof; (b) polyhydric alcohols having from 2 to 10 carbon atoms and the monoesters thereof, the diesters thereof, the monoethers thereof, the homopolymers thereof, and the homopolymer monoethers thereof; (c) saturated and unsaturated fatty acids having from 8 to 20 carbon atoms and the alkyl esters thereof; (d) absorbent solids selected from the group consisting of carbon black, silica, and molecular sieves; (e) ultraviolet screening materials; and (f) combinations thereof;
said particle selected from the group consisting of an insecticide, a fertilizer, a trace mineral, an acaricide, a nematicide, a molluscicide, a herbicide, a fungicide, a pheromone, an odorant, a fragrance, an attractant, a repellent, a plant regulant, and combinations thereof.

24. An encapsulated particle having been in situ encapsulated and concurrently and directly adhered to an earth target, comprising:
a particle system and a wall system, said wall system comprising a polymer film encapsulating said core system,
said polymer film having been made from a colloidal or an emulsion dispersion type polymer, said particle and wall system having been made from a dispersion comprising by weight from about 0.1 percent to about 25 percent of a film-forming polymer having a molecular weight greater than 300,000 and capable of encapsulating a particle by coacervation, from about 35 percent to about 99 percent of a liquid, and from about 1 percent to about 40 percent of a particle, or from about 0.01 to about 40 percent when said particle is a pheromone, said particle being soluble or dispersible in said solvent;

said liquid being a compound in which said polymer is dispersible.

25. An encapsulated particle according to claim 24, wherein said polymer is selected from the group consisting of (a) an acrylic type polymer of a copolymer comprising a polymer or copolymer made from monomers having the formula where $R_4$ is hydrogen or an alkyl, cycloalkyl, aryl, or aralkyl having from 1 to 30 carbon atoms and $R_5$ is hydrogen or an alkyl, cycloalkyl, aryl, or aralkyl having from 1 to 12 carbon atoms; (b) the salt of (1) an interpolymer having the structure wherein R and $R_1$ are members of the group consisting of hydrogen and methyl, $R_2$ is a member of the group consisting of methyl and ethyl; n represents from 3 to 12 weight percent based on the combined weight of n, x, y and z, x represents from 8 to 25 percent based on the combined weight of n, x, y and z; y represents from 45 to 89 weight percent based on the combined weight of n, x, y and z; z represents from 0 to 44 weight percent based on the combined weight of n, x, y and z; the sum of the numerical value of n+x+y+z is always exactly 100 and the groups n, x, y and z are present in a heterogeneous relative position, and (2) a member of the group consisting of ammonia, hydrazine, a low boiling primary aliphatic amine and a low boiling secondary aliphatic amine, said salt being soluble in water in the pH range of from about 5 to 8; and (c) combinations thereof; and wherein said liquid is selected from the group consisting of alcohols having from 1 to 5 carbon atoms, acetone, diisobutyl ketone, methyl ethyl ketone, dioxane, methylene chloride, water, and combinations thereof.

26. An encapsulated particle according to claim 25, wherein said particle is selected from the group consisting of an insecticide, a fertilizer, a trace mineral, an acaricide, a nematicide, a molluscicide, a herbicide, a fungicide, a pheromone, an odorant, a fragrance, an attractant, a repellent, a plant regulant, and combinations thereof.

27. An encapsulated particle according to claim 26, wherein said trace mineral is selected from the group consisting of zinc chloride, zinc sulfate, ferric chloride, ferric sulfate, copper sulfate, copper oxychloride, boric acid, sodium borate, sodium selenate, cobalt sulfate, sodium molybdate, manganese sulfate, manganese chloride, and combinations thereof; wherein said insecticide and said acaricide is selected from the group consisting of O,O-diethyl-O-p-nitrophenyl phosphorothioate (Parathion), O,O-dimethyl-O-p-nitrophenyl phosphorothioate (Methyl parathion), O,O-dimethyl-O-(3-methyl-4-nitrophenyl)phosphorothioate (Sumithion), O,O-diethyl-O-(2-isopropyl-6-methyl-5-pyrimidinyl) phosphorothioate (Diazinon), O,O-dimethyl-O-[3-methyl-4-(methylthio)phenyl] phosphorothioate (Fenthion), Pyrethrin-piperonyl butoxide, pyrethroids, 1-naphthyl methylcarbamate (Carbaryl), 2-(1-methylethoxy)phenyl methylcarbamate (Baygon), 2-methyl-2-(methylthio) propionaldehyde-O-(methyl carbamonyl) oxime (Aldicarb), S-methyl N-[methylcarbamonyl(oxy)] thioacetamine (lannate), chlorinated camphene, 67 percent octachlorocamphene (Toxaphene), tricalcium arsenate, sodium aluminum fluoride, Dichlorodiphenyltrichloroethane, tricyclohexyltin hydroxide (Plictran), and combinations thereof; wherein said Nematicide is selected from the group consisting of O,O-diethyl-O-2,4-dichlorophenyl phosphorothioate(dichlorofenthion), O-ethyl-S,S-dipropyl phosphorodithioate (Ethoprop), N,N-dimethyldodecanamide, and combinations thereof; wherein said molluscicide is selected from the group consisting of copper sulfate, n-tritylmorpholine (trifenmorph), tributyltin fluoride, sodium pentachlorophenate, niclosamide, and combinations thereof; wherein said herbicide is selected from the group consisting of 2,4-dichlorophenoxyacetic acid (2,4-D), alkylamine salts of 2,4-D, butoxyethanol ester of 2,4-D, 2,4,5-trichlorophenoxyacetic acid (2,4,5-T), 2-(2,4,5-trichlorophenoxy)priopionic acid (Silvex), 3-amino-2,5-dichlorobenzoic acid (chloramben), 3,6-dichloro-O-anisic acid (Dicamba), 2,3,5-trichlorophenylacetic acid (Fenac), 2,6-dichlorobenzonitril (Dichlobenil), N,N-diallyl-2-chloroacetamine (Randox), S-ethyl diisobutylthiocarbamate (Sutan), isopropyl N-(3-chlorophenyl) carbamate (chloropropham), 3-amino-1,2,4-triazole (Amitrole), 2-chloro-4,6-Bis(ethylamino)-isopropylamino-S-triazine (Atrazine), 6,7-dihydrodipyrido(1,2-a; 2', 1'-c)pyrazinediium dibromide (Diquat), and combinations thereof; and wherein said fungicide is selected from the group consisting of triphenyltin acetate, methyl-1-(butacarbamoyl)-2-benzimidazole carbamate (Benomyl), hexachloraphene, and combinations thereof.

28. An encapsulated particle according to claim 27, wherein the amount of said polymer ranges from about 4 percent to about 13 percent by weight, wherein the amount of said liquid ranges from about 50 percent to about 90 percent by weight, and wherein the amount of said particle ranges from about 5 percent to about 30 percent by weight, or from about 0.05 percent to about 10 percent when said particle is a pheromone.

29. An encapsulated particle according to claim 24, 25, 26, 27, or 28, wherein said salt of said interpolymer has a molecular weight ranging from about 300,000 to about 3,000,000, and wherein said acrylic polymer has a molecular weight ranging from about 400,000 to about 4,000,000.

30. An encapsulated particle according to claim 29, further comprising crosslinking agents for reaction with said polymer and including an alkaline compound so that the pH of said solution ranges from about 6.5 to about 8.0, said crosslinking agent being an alkaline earth salt, a urea, diamines, triamines, diamides, or triamides, said alkaline earth salt selected from the group consisting of calcium, barium, beryllium and magnesium, said anion portion of said salt selected from the group consisting of carbonate, bicarbonate, oxide, hydroxide, nitrate, $F^-$, $Cl^-$, $I^-$, $Br^-$, the amount of said crosslinking agent ranging from about 0.01 to about 1 percent by weight based upon the total weight of said formulation.

31. An encapsulated particle according to claim 29, including an adhesive agent.

32. An encapsulated particle according to claim 29, including from about 1 percent to about 40 percent of a core agent for modifying the solubility, the ultraviolet degradation, and the volatility of said particle with said polymer upon encapsulation, said core agent selected from the group consisting of (a) monohydric alcohols having from 6 to 20 carbon atoms and the mono- and polyunsaturated derivatives thereof; (b) polyhydric alcohols having from 2 to 10 carbon atoms and the monoesters thereof, the diesters thereof, the triesters thereof, the monoethers thereof, the homopolymers thereof, and the homopolymer monoethers thereof; (c) saturated and unsaturated fatty acids having from 8 to 20 carbon atoms and the alkyl esters thereof; (d) absorbent solids selected from the group consisting of carbon black, silica, and molecular sieves; (e) ultraviolet screening materials; (f) soy oil; and (g) combinations thereof.

33. An encapsulated particle according to claim 29, including a film modifying polymer.

34. An in situ self-encapsulating polymeric containing formulation for concurrent and direct application to an earth target, comprising by weight, based upon the total weight of said formulation from about 0.1 percent to about 25 percent of a film-forming polymer capable of encapsulating a particle by coacervation, from about 35 percent to about 99 percent of a liquid, and from about 1 percent to about 40 percent of a particle or from about 0.01 percent to about 40 percent when said particle is a pheromone, said particle being soluble or dispersible in said liquid, said liquid being a compound in which said polymer is soluble, and from about 1 percent to about 40 percent by weight of a core agent.

35. A formulation according to claim 34, including from about 0.1 percent to about 10 percent by weight of a film-modifying polymer.

36. A process for the in situ encapsulation of particles between a spraying apparatus and an earth target, comprising the steps of:

(a) preparing a self-encapsulating polymer-containing solution;

said solution comprising by weight from about 0.1 percent to about 25 percent of a film-forming polymer capable of encapsulating a particle by coacervation, from about 35 percent to about 99 percent of a liquid, said liquid being a compound which will dissolve said polymer, and from about 1 percent to about 40 percent of particles, or from about 0.01 percent to about 40 percent when said particle is a pheromone, said particle being soluble or dispersible in said solvent;

in situ encapsulating said soluble or dispersible particle by:

spraying into the earth's atmosphere said dispersion containing said soluble or dispersible particle from a spray apparatus, and immediately thereafter;

evaporating said solvent in said earth's atmosphere and coacervating during the passage from said spraying apparatus to an earth target said polymer and said particle in said earth's atmosphere so that said polymer substantially encapsulates said particle; and concurrently and directly applying said encapsulated particle to an earth target.

37. A process according to claim 36, including adding from about 0.1 to about 10 percent by weight of a film-modifying polymer.

* * * * *